US00PP24913P2

(12) United States Plant Patent
Darby

(10) Patent No.: US PP24,913 P2
(45) Date of Patent: Sep. 23, 2014

(54) HOP PLANT NAMED 'SUMNER'

(50) Latin Name: *Humulus lupulus*
Varietal Denomination: Sumner

(71) Applicant: Peter Darby, East Maillin (GB)

(72) Inventor: Peter Darby, East Maillin (GB)

(73) Assignee: East Malling Research Ltd., East Malling, Kent (GB)

( * ) Notice: Subject to any disclaimer, the term of this patent is extended or adjusted under 35 U.S.C. 154(b) by 17 days.

(21) Appl. No.: 13/694,958

(22) Filed: Jan. 22, 2013

(51) Int. Cl.
*A01H 5/00* (2006.01)

(52) U.S. Cl.
USPC ..... Plt./236

(58) Field of Classification Search
USPC ..... Plt./236
See application file for complete search history.

*Primary Examiner* — Anne Grunberg
(74) *Attorney, Agent, or Firm* — C. A. Whealy

(57) ABSTRACT

A new and distinct cultivar of Hop plant named 'Sumner', characterized by its upright and relatively compact plant habit; freely branching habit; stems reddish brown in color during the late summer and autumn; and attractive lime green to yellow green-colored leaves.

2 Drawing Sheets

Botanical designation: *Humulus lupulus.*
Cultivar denomination: 'SUMNER'.

BACKGROUND OF THE INVENTION

The present invention relates to a new and distinct cultivar of Hop plant, botanically known as *Humulus lupulus*, commercially grown for its ornamental value, and hereinafter referred to by the name 'Sumner'.

The new Hop plant is a product of a planned breeding program conducted by the Inventor in Wye, Kent, United Kingdom. The objective of the breeding program was to develop compact Hop plants with high alpha acids and desirable aroma.

The new Hop plant originated from a cross-pollination conducted by the Inventor in July, 1998 of a proprietary selection of *Humulus lupulus* identified as code number 35/96/7, not patented, as the female, or seed, parent with a proprietary selection of *Humulus lupulus* identified as code number 15/92/2, not patented, as the male, or pollen, parent. The new Hop plant was discovered and selected by the Inventor in September, 2000 as a single female plant from within the progeny of the stated cross-pollination in a controlled environment in Wye, Kent, United Kingdom.

Asexual reproduction of the new Hop plant by softwood cuttings since June, 2002 in Wye, Kent, United Kingdom has shown that the unique features of this new Hop plant are stable and reproduced true to type in successive generations of asexual reproduction.

SUMMARY OF THE INVENTION

Plants of the new Hop have not been observed under all possible environmental conditions and cultural practices. The phenotype may vary somewhat with variations in environmental conditions such as temperature, daylength and light intensity without, however, any variance in genotype.

The following traits have been repeatedly observed and are determined to be the unique characteristics of 'Sumner'. These characteristics in combination distinguish 'Sumner' as a new and distinct Hop plant:

1. Upright and relatively compact plant habit.
2. Freely branching habit.
3. Stems reddish brown in color during the late summer and autumn.
4. Attractive lime green to yellow green-colored leaves.

In side-by-side comparisons conducted in Wye, Kent, United Kingdom, plants of the new Hop differ primarily from plants of the parent selections in the following characteristics:

1. Plants of the new Hop grow slower than plants of the parent selections.
2. Plants of the new Hop and the parent selections differ in leaf color as plants of the parent selections have green-colored leaves.

Plants of the new Hop can be compared to plants of the *Humulus lupulus* 'Aurea', not patented. In side-by-side comparisons, plants of the new Hop differed primarily from plants of 'Aurea' in the following characteristics:

1. Plants of the new Hop grew more slowly than and were not as vigorous as plants of 'Aurea'.
2. Plants of the new Hop and 'Aurea' differed in leaf shape as plants of the Hop had dimorphic leaves, that is, plants of the new Hop had leaves that were either narrowly ovate with cordate tendencies or palmately-lobed whereas plants of 'Aurea' only had palmately-lobed leaves.

BRIEF DESCRIPTION OF THE PHOTOGRAPHS

The accompanying colored photographs illustrate the overall appearance of the new Hop plant showing the colors as true as it is reasonably possible to obtain in colored reproductions of this type. Colors in the photographs may differ slightly from the color values cited in the detailed botanical description which accurately describe the colors of the new Hop plant.

The photograph on the first sheet comprises a side perspective view of a typical flowering plant of 'Sumner' grown in an outdoor nursery.

The photograph on the second sheet is a close-up view of typical leaves of 'Sumner'.

DETAILED BOTANICAL DESCRIPTION

The aforementioned photographs, following observations and measurements describe plants grown during the summer in an outdoor nursery in Grand Haven, Mich. and under cultural practices typical of commercial Hop production. Plants were three years old when the photographs and description were taken. In the following description, color references are made to The Royal Horticultural Society Colour Chart, 2001 Edition, except where general terms of ordinary dictionary significance are used.

Botanical classification: *Humulus lupulus* 'Sumner'.

Commercial use: Plants of the new Hop were selected on the basis of its ornamental value and not for its use in brewing.

Parentage:

- *Female or seed, parent*.—Proprietary selection of *Humulus lupulus* identified as code number 35/96/7, not patented.
- *Male or pollen, parent*.—Proprietary selection of *Humulus lupulus* identified as code number 15/92/2, not patented.

Propagation:

- *Type*.—By softwood cuttings.
- *Time to initiate roots, summer*.—About one month at temperatures of 20° C.
- *Time to produce a rooted young plant, summer*.—About four months at temperatures of 20° C.
- *Root description*.—Fine to medium in thickness, somewhat fibrous and somewhat fleshy.
- *Rooting habit*.—Freely branching; dense.

Plant description:

- *Plant and growth habit*.—Herbaceous perennial twining plant; upright and relatively compact plant habit; moderate growth rate; vigorous growth habit; dioecious.
- *Branching habit*.—Freely branching habit with about 16 branches developing per plant; pinching enhances lateral branch development.
- *Plant height*.—About 2.5 meters.
- *Plant diameter*.—About one meter.

Lateral branch description:

- *Length*.—About 40 cm.
- *Diameter*.—About 2 mm.
- *Internode length*.—About 4.5 cm.
- *Texture*.—Pubescent.
- *Strength*.—Strong.
- *Color, developing*.—Close to 149A.
- *Color, fully developed*.—Close to 166A and 176A.
- *Color, late summer and autumn*.—Close to 166A.

Foliage description:

- *Arrangement*.—Opposite; simple.
- *Length*.—About 5.5 cm.
- *Width*.—About 4 cm.
- *Shape*.—Dimorphic; leaves are either narrowly ovate with cordate tendencies or palmate with three lobes.
- *Apex*.—Acute.
- *Base*.—Cordate.
- *Margin*.—Serrate to dentate.
- *Texture, upper surface*.—Pubescent.
- *Texture, lower surface*.—Pubescent with prickles along the midvein.
- *Venation pattern*.—Pinnate.
- *Color*.—Developing leaves, upper and lower surfaces: Between 149C and 150C. Fully expanded leaves, upper surface: Close to 150B; venation, close to 150C. Fully expanded leaves, lower surface: Close to 149B; venation, close to 149B.
- *Petiole*.—Length: About 2 cm. Diameter: About 2 mm. Texture, upper surface: Pubescent. Texture, lower surface: Pubescent; prickles along the veins. Color, upper and lower surfaces: Close to 144A.

Flower description:

- *Flower arrangement and habit*.—Imperfect female flowers (also known as hops) and arranged on short, congested, bracted terminal spikes; spikes cone-like with typically about 12 to 24 flowers per inflorescence; flowers face upright to outwardly; flowers without petals or sepals.
- *Fragrance*.—Moderately fragrant, pleasant.
- *Natural flowering season*.—Plants of the new Hop flower during July and August in the United Kingdom.
- *Flower longevity*.—Flowers last about three to four weeks on the plant; flowers persistent.
- *Inflorescence height*.—About 1.8 cm.
- *Inflorescence diameter*.—About 1 cm.
- *Flower diameter*.—About 1 mm.
- *Flower depth (height)*.—About 2.4 mm.
- *Inflorescence buds*.—Length: About 3 mm. Diameter: About 2 mm. Shape: Oblong. Color: Close to 146B.
- *Spike bracts*.—Quantity and arrangement: About 12 to 16 whorled around the spike. Length: About 5 mm. Width: About 3 mm. Shape: Subulate. Apex: Acute. Base: Cuneate. Margin: Entire. Texture, upper and lower surfaces: Pubescent. Color: When opening, upper and lower surfaces: Close to 146B. Fully opened, upper and lower surfaces: Close to 146B.
- *Pedicels*.—Length: About 1.3 cm to 2 cm. Diameter: About 2 mm. Strength: Strong. Aspect: About 20° to 30° from spike axis. Texture: Smooth, glabrous. Color: Close to 189A.
- *Reproductive organs*.—Stamens: None observed on female flowers. Pistils: Quantity: One per flower. Pistil length: About 3.5 cm. Style length: About 3.4 cm. Style color: Close to 145C. Stigma color: Close to 145C. Ovary color: Close to 145C. Seeds and fruits: Seed and fruit development have not been observed on plants of the new Hop.

Pathogen & pest resistance: Plants of the new Hop have not been observed to be resistant to pests and pathogens common to Hop plants.

It is claimed:

1. A new and distinct Hop plant named 'Sumner' as illustrated and described.

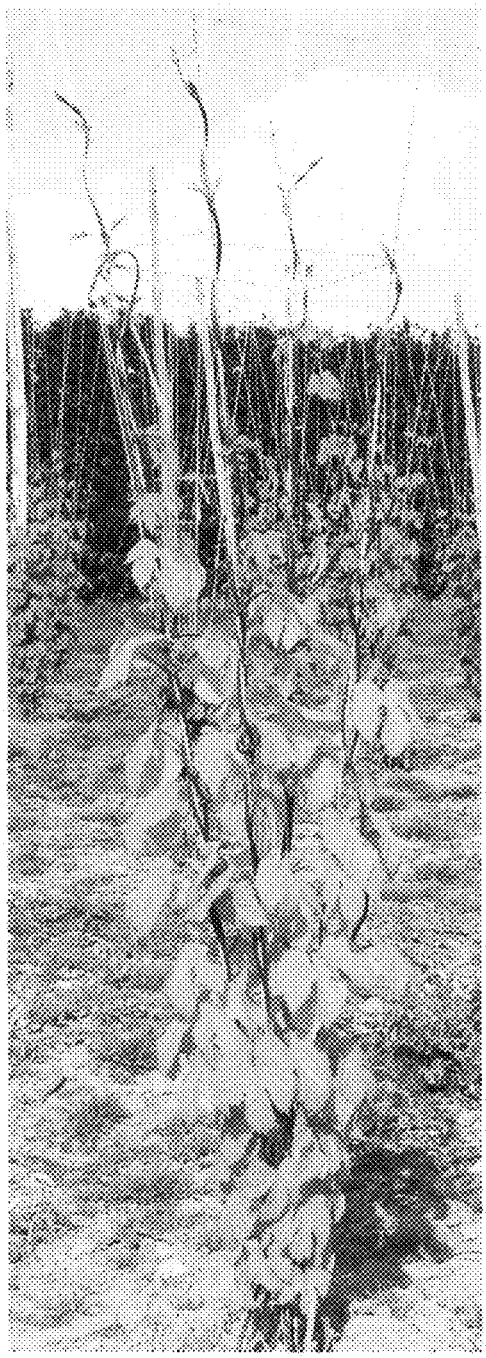

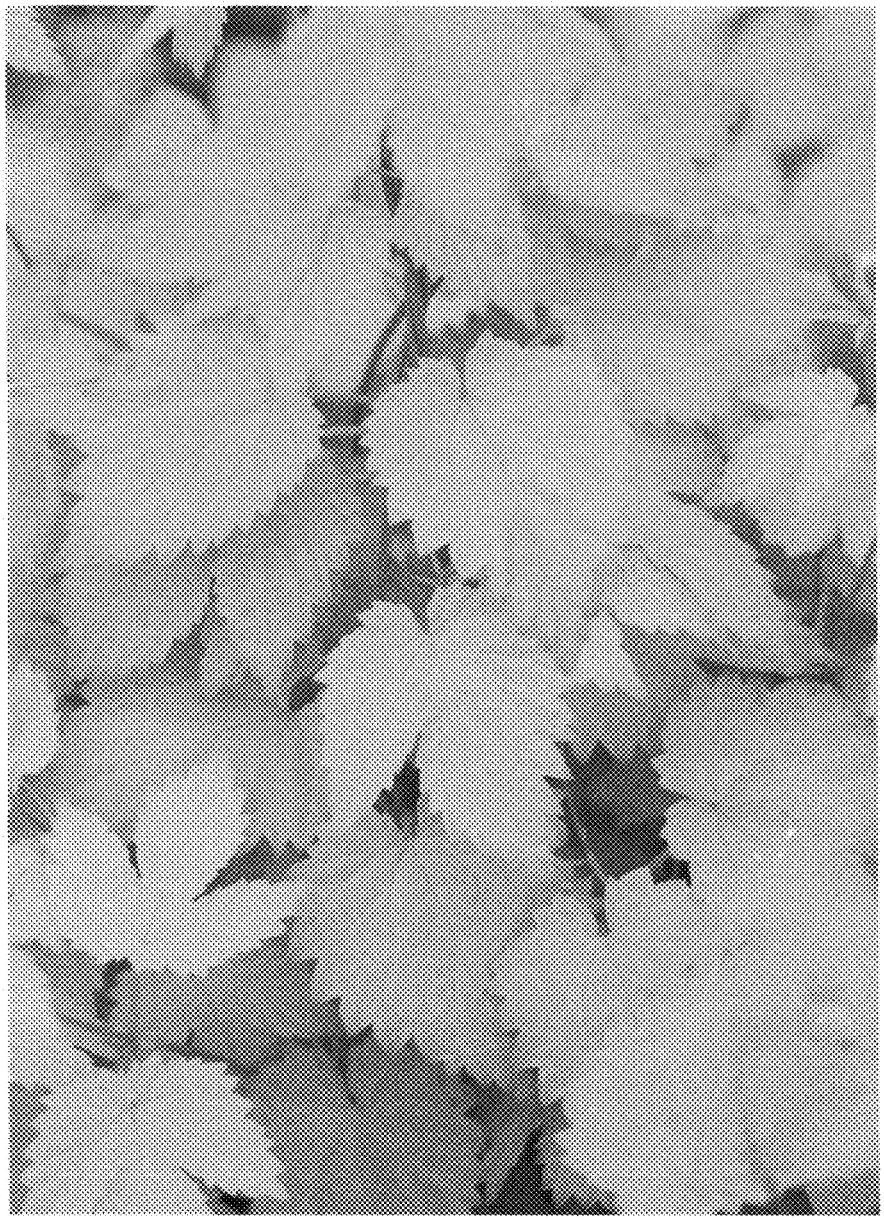

* * * * *